(12) United States Patent
Flohr et al.

(10) Patent No.: US 9,358,197 B2
(45) Date of Patent: *Jun. 7, 2016

(54) METHOD EMPLOYING POLYOLS WHEN CHEMICALLY MODIFYING THE INTERNAL REGION OF A HAIR SHAFT

(71) Applicant: The Procter & Gamble Company, Cincinnati, OH (US)

(72) Inventors: Andreas Flohr, Kronberg im Taunus (DE); Thomas Kripp, Frankisch-Crumbach (DE); Sonja Rodriguez Bares, Singapore (SG)

(73) Assignee: The Procter & Gamble Company, Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/918,061

(22) Filed: Jun. 14, 2013

(65) Prior Publication Data

US 2014/0041678 A1    Feb. 13, 2014

(30) Foreign Application Priority Data

Jun. 15, 2012  (EP) .................................. 12172116.1
Jun. 6, 2013   (EP) .................................. 13170778.8
Jun. 6, 2013   (WO) ................ PCT/US2013/044405

(51) Int. Cl.
*A61Q 5/04*   (2006.01)
*A61Q 5/12*   (2006.01)
*A61K 8/46*   (2006.01)
*A61K 8/86*   (2006.01)

(52) U.S. Cl.
CPC . *A61K 8/466* (2013.01); *A61K 8/86* (2013.01); *A61Q 5/04* (2013.01); *A61K 2800/95* (2013.01); *A61Q 5/12* (2013.01)

(58) Field of Classification Search
None
See application file for complete search history.

(56) References Cited

U.S. PATENT DOCUMENTS

| | | |
|---|---|---|
| 3,472,243 A | 10/1969 | Wall |
| 3,472,604 A | 10/1969 | Dasher |
| 3,475,114 A | 10/1969 | Bolinger |
| 3,537,809 A | 11/1970 | Cednas |
| 3,583,408 A | 6/1971 | Wall |
| 3,619,114 A | 11/1971 | Anzuino |
| 3,619,117 A | 11/1971 | Anzuino |
| 3,619,118 A | 11/1971 | Anzuino |
| 3,633,591 A | 1/1972 | Anzuino |
| 3,634,022 A | 1/1972 | Robbins |
| 3,661,161 A | 5/1972 | Kalopissis |
| 3,676,550 A | 7/1972 | Anzuino |
| 3,678,157 A | 7/1972 | Kalopissis |
| 3,820,550 A | 6/1974 | Kinney |
| 3,882,114 A | 5/1975 | Kalopissis |
| 3,909,195 A | 9/1975 | Machell |
| 4,152,416 A | 5/1979 | Marra |
| 4,278,659 A | 7/1981 | Breuer |
| 4,338,295 A | 7/1982 | Highley |
| 4,588,760 A | 5/1986 | Jachowicz |
| 4,719,104 A | 1/1988 | Patel |
| 4,726,945 A | 2/1988 | Patel |
| 5,002,761 A | 3/1991 | Mueller |
| 5,362,486 A | 11/1994 | Nandagiri |
| 6,482,808 B1 | 11/2002 | Grasser |
| 6,709,648 B2 | 3/2004 | Sako |
| 6,740,317 B1 | 5/2004 | Cho |
| 7,255,869 B2 | 8/2007 | Uchida |
| 7,981,167 B2 | 7/2011 | Carballada |
| 8,048,846 B2 | 11/2011 | Chahal |
| D658,009 S | 4/2012 | Davis |
| D681,344 S | 5/2013 | McNeill |
| 2003/0103930 A1 | 6/2003 | Uchida |
| 2003/0175229 A1 | 9/2003 | Giroud |
| 2004/0016062 A1 | 1/2004 | Plos |
| 2004/0166071 A1 | 8/2004 | Pfaffernoschke |
| 2004/0261198 A1 | 12/2004 | Kainz |
| 2006/0237696 A1* | 10/2006 | Gourlaouen et al. ......... 252/500 |
| 2007/0066506 A1 | 3/2007 | Behler |
| 2007/0275020 A1 | 11/2007 | Lendlein |
| 2007/0277332 A1 | 12/2007 | Bimczok |
| 2008/0187506 A1 | 8/2008 | Carballada |
| 2008/0210253 A1 | 9/2008 | Carballada |
| 2008/0311050 A1 | 12/2008 | Lendlein |

(Continued)

FOREIGN PATENT DOCUMENTS

| | | |
|---|---|---|
| DE | 10259199 A1 | 6/2004 |
| JP | S62209006 A | 9/1987 |
| JP | H04208214 A | 7/1992 |
| JP | H10279436 A | 10/1998 |
| WO | WO0045777 A1 | 8/2000 |
| WO | WO0213773 A2 | 2/2002 |
| WO | WO0245665 A1 | 6/2002 |
| WO | WO2004043330 A2 | 5/2004 |
| WO | WO2004062633 A1 | 7/2004 |

OTHER PUBLICATIONS

Anonymous: Carbowax™ Polyethylene Glycols Innovation, Performance, Flexibility and Quality from the Global Leader in PEGs; Oct. 2011.
Database GNPD; Mintel: Herbal Hair Moisturiser, Aug. 2001.
PCT International Search Report and Written Opinion for PCT/US2013/044405 dated Aug. 7, 2014.

*Primary Examiner* — Jyothsna Venkat
(74) *Attorney, Agent, or Firm* — James T. Fondriest

(57) ABSTRACT

A method for chemically modifying the internal region of the hair shaft comprising applying a monomer composition to the hair, wherein the monomer composition comprises an ethylenic monomer having a molecular weight of 500 g/mole or less; then rinsing the hair; then applying a conditioning composition to the hair, wherein the conditioning composition comprises a hydrophobic polyol and a hydrophilic polyol; and wherein the method comprises applying an initiator to the hair prior to rinsing the hair, wherein the initiator initiates the chemical modification.

1 Claim, 8 Drawing Sheets

(8 of 8 Drawing Sheet(s) Filed in Color)

(56) References Cited

U.S. PATENT DOCUMENTS

| | | |
|---|---|---|
| 2009/0022681 A1 | 1/2009 | Carballada |
| 2010/0028279 A1* | 2/2010 | Carballada et al. .......... 424/70.1 |
| 2010/0028286 A1 | 2/2010 | Carballada |
| 2011/0064684 A1 | 3/2011 | Krause |
| 2011/0070179 A1 | 3/2011 | Puerta |
| 2011/0126850 A1 | 6/2011 | Hoffmann |
| 2011/0229429 A1 | 9/2011 | Hoffmann |
| 2012/0180807 A1 | 7/2012 | Flohr |
| 2012/0183486 A1 | 7/2012 | Flohr |
| 2013/0058882 A1 | 3/2013 | Flohr |

* cited by examiner

METHOD EMPLOYING POLYOLS WHEN CHEMICALLY MODIFYING THE INTERNAL REGION OF A HAIR SHAFT

FIELD OF THE INVENTION

A method for chemically modifying the internal region of the hair shaft comprising: applying a monomer composition to the hair, wherein the monomer composition comprises an ethylenic monomer having a molecular weight of 500 g/mole or less; then rinsing the hair; then applying a conditioning composition to the hair, wherein the conditioning composition comprises a hydrophobic polyol and a hydrophilic polyol; and wherein the method comprises applying an initiator to the hair prior to rinsing the hair, wherein the initiator initiates the chemical modification.

BACKGROUND OF THE INVENTION

Methods for chemically modifying the internal region of the hair shaft are already known. WO2009/088520A1 and EP-A-2295029 describe the use of ethylenic monomers to chemically modify the internal region of the hair shaft—in particular the ethylenic molecules may bond to the hair and/or to each other to form larger molecules e.g. polymers inside the hair. This increases the rigidity of the hair via the modification of the internal structure of the hair shaft, which provides styling advantages e.g. allowing style formation or increased volume and style retention longer periods of time.

Such methods typically involve a number of steps. Washing the hair with the clarifying shampoo as an initial step is usually carried out and then, after the chemical modification reaction time is complete, a second washing step is normally employed. Consumers thus almost always want a final conditioning step in order to provide more consumer-acceptable hair feel, freer combing, detangling, reduced hair friction, cleaner hair feel.

There is a need, however, for methods providing conditioning tailored to the methods for chemically modifying the internal region of the hair shaft. In other words, conditioning that enhances and/or is more complementary to the improved mechanical properties provided by the chemical modifying. There is also a need for methods providing conditioning that reduces or nullifies any undesirable results of the chemical modifying. Furthermore, there is a need for methods providing conditioning that do not have any of the drawbacks of conventional conditioners used after chemical modification of the hair.

SUMMARY OF THE INVENTION

According to a first aspect, the present invention relates to a method for chemically modifying the internal region of the hair shaft, comprising:
  (a) applying a monomer composition to the hair, wherein the monomer composition comprises an ethylenic monomer having a molecular weight of 500 g/mole or less; then
  (b) rinsing the hair; then
  (c) applying a conditioning composition to the hair, wherein the conditioning composition comprises a hydrophobic polyol and a hydrophilic polyol;
and wherein the method comprises applying an initiator to the hair prior to rinsing the hair (b), wherein the initiator initiates the chemical modification.

According to a second aspect, the present invention relates to a kit for chemically modifying the internal region of the hair shaft comprising:
  (I). an oxidising composition, wherein the oxidising formulation comprises an oxidising agent being hydrogen peroxide;
  (II). a monomer composition, wherein the monomer composition comprises an ethylenic monomer having a molecular weight of 500 g/mole or less;
  (III). a conditioning composition to the hair, wherein the conditioning composition comprises a hydrophobic polyol and a hydrophilic polyol.

According to a third aspect, the present invention relates to the use of the kit according to the second aspect, for chemically modifying the internal region of the hair shaft.

BRIEF DESCRIPTION OF THE DRAWINGS

The patent or application file contains at least one photograph executed in color. Copies of this patent or patent application publication with color photographs will be provided by the Office upon request and payment of the necessary fee.

Hair strands are treated with different methods and then tested for static. In test A, the hair is stroked with the fingers after treatment (A1, before stroking; A2, after stroking). In test B, the hair is combed after treatment (B1, before combing; B2, after combing).

FIGS. 1A1, 1A2, 1B1, and 1B2: No chemical modification, no conditioning step.

FIGS. 2A1, 2A2, 2B1, and 2B2: Chemical modification, no conditioning step.

FIGS. 3A1, 3A2, 3B1, and 3B2: Chemical modification, conditioning step where conditioner comprises: 93% water; 2% hydrogen peroxide; 3% cetearyl alcohol; and the following components in amounts each being 2% or less: Ceteareth-25; Polyquaternium-35; Cetrimonium Chloride.

FIGS. 4A1, 4A2, 4B1, and 4B2: Chemical modification, conditioning step where conditioning composition is pursuant to the present invention (conditioning composition comprises: 52% PEG-4; 19% PPG-34; 15% anhydrous magnesium sulfate; 4% dimethicone [12 500 cSt]; and the following components in amounts each being 2% or less: hydroxypropyl cellulose; Behentrimonium Chloride [in isopropanol]; Cetrimonium Chloride; cetyl alcohol; stearyl alcohol; PEG/PPG-300/55 Copolymer; dioleoyl ethyl hydroxyethylmonium methosulfate).

FIGS. 5A1, 5A2, 5B1, and 5B2: Chemical modification, conditioning step where conditioning composition is pursuant to the present invention (conditioning composition is as per FIGS. 4A1, 4A2, 4B1, and 4B2 except the conditioning composition was diluted by half with water).

FIGS. 6A1, 6A2, 6B1, and 6B2: Chemical modification, conditioning step where as the conditioning step, an aqueous solution comprising 15% magnesium sulfate was applied to the hair.

FIGS. 7A1, 7A2, 7B1, and 7B2: Chemical modification, conditioning step where conditioning composition is pursuant to the present invention (conditioning composition comprises 52 parts PEG-4 and 19 parts PPG-34).

FIG. 8A is the blank.

DETAILED DESCRIPTION OF THE INVENTION

General and Definitions

Figure 1:
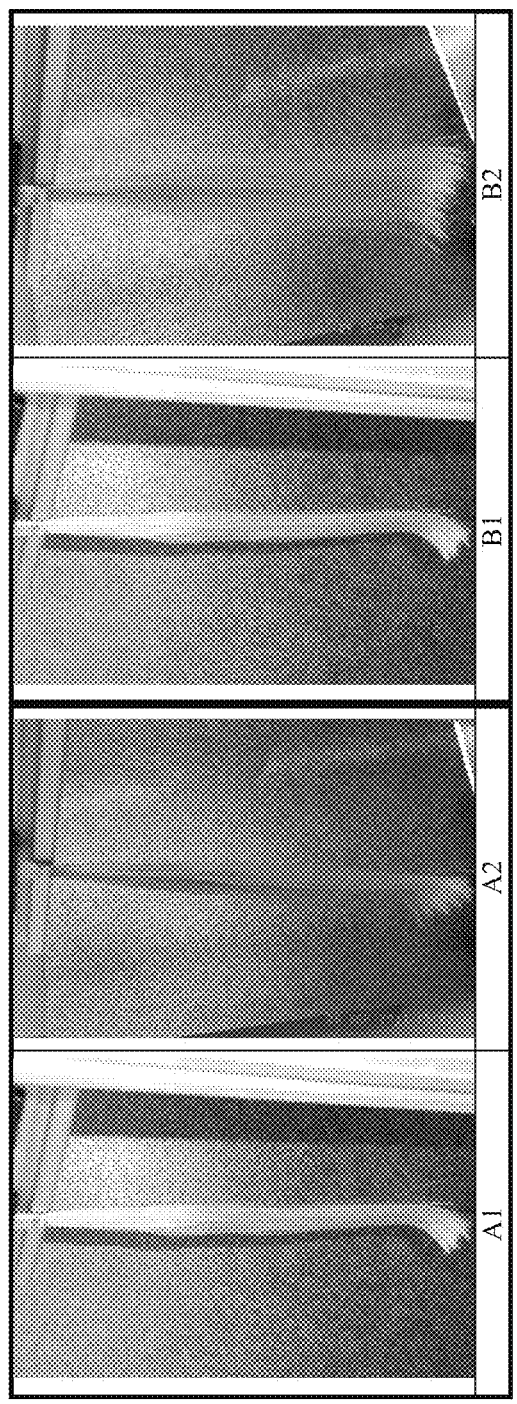
Figure 2:
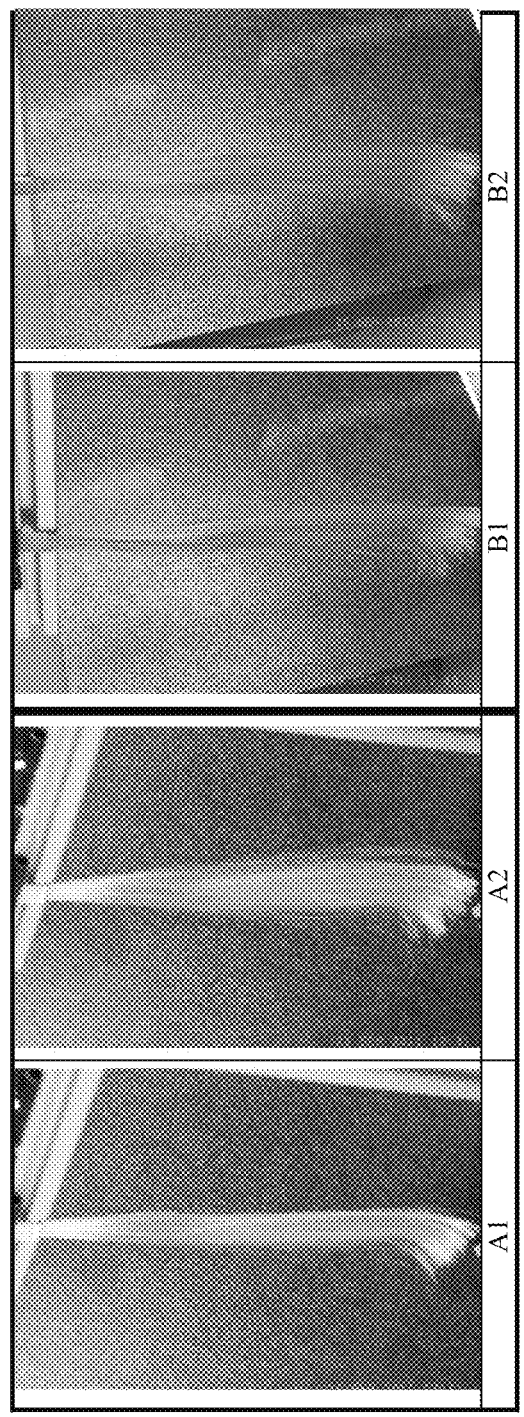
Figure 3:
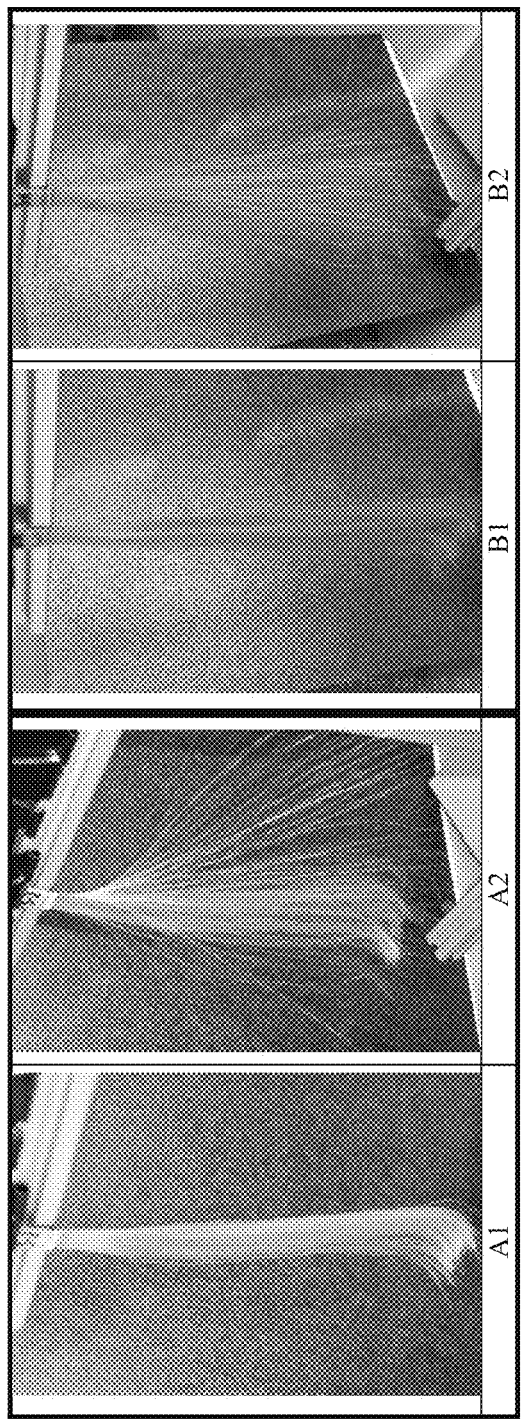
Figure 4:
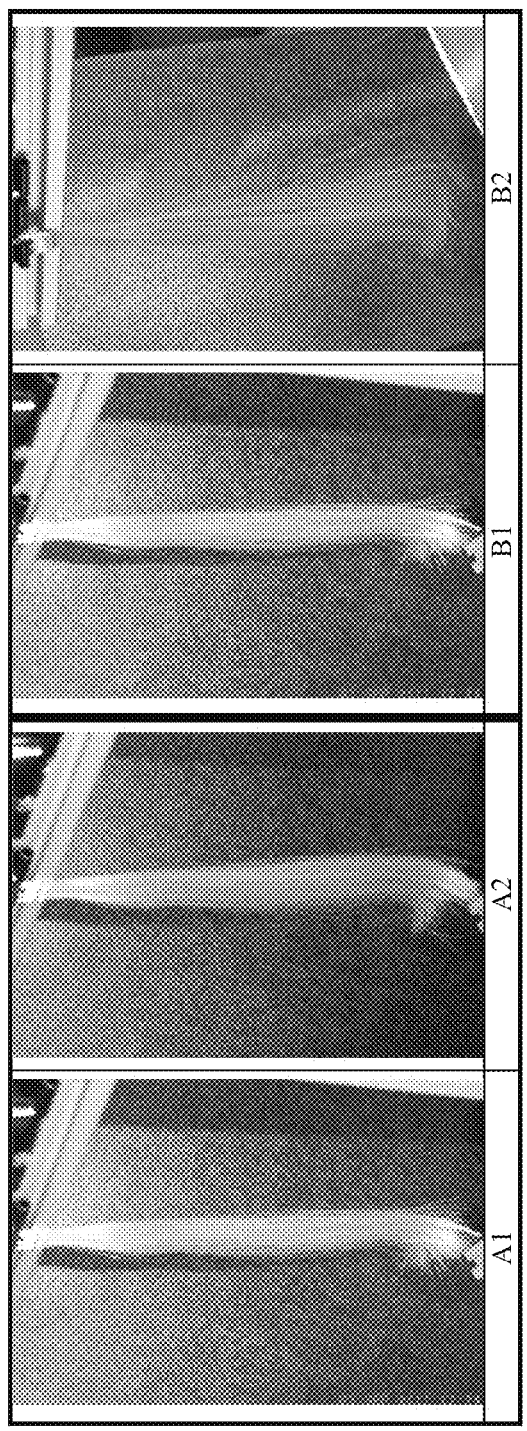
Figure 5:
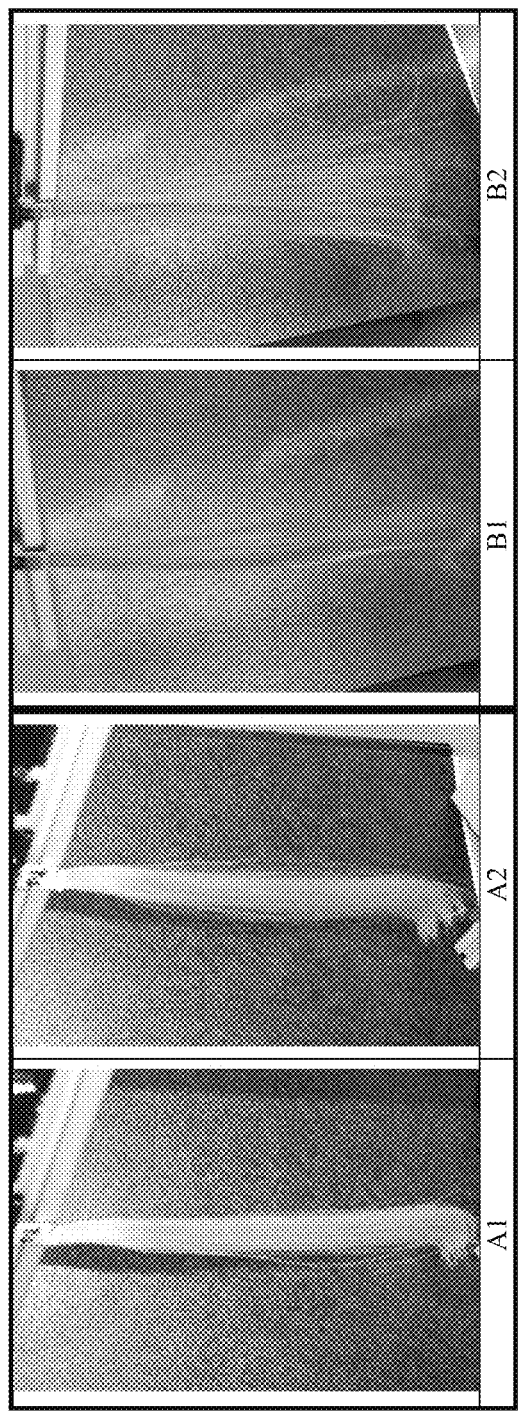
Figure 6:
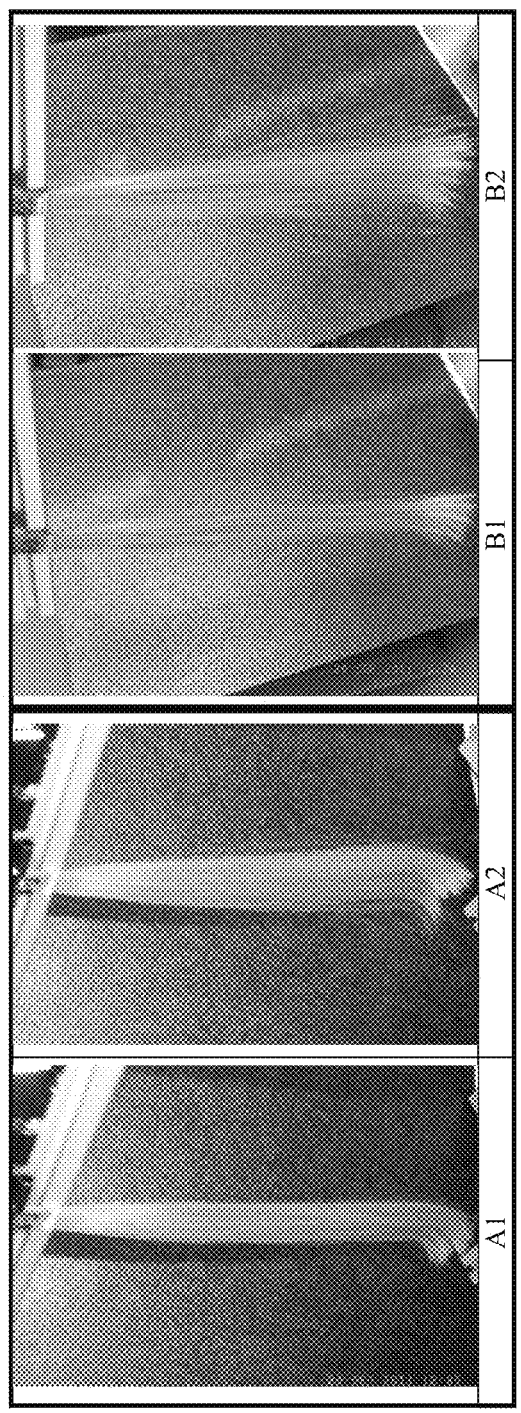
Figure 7:
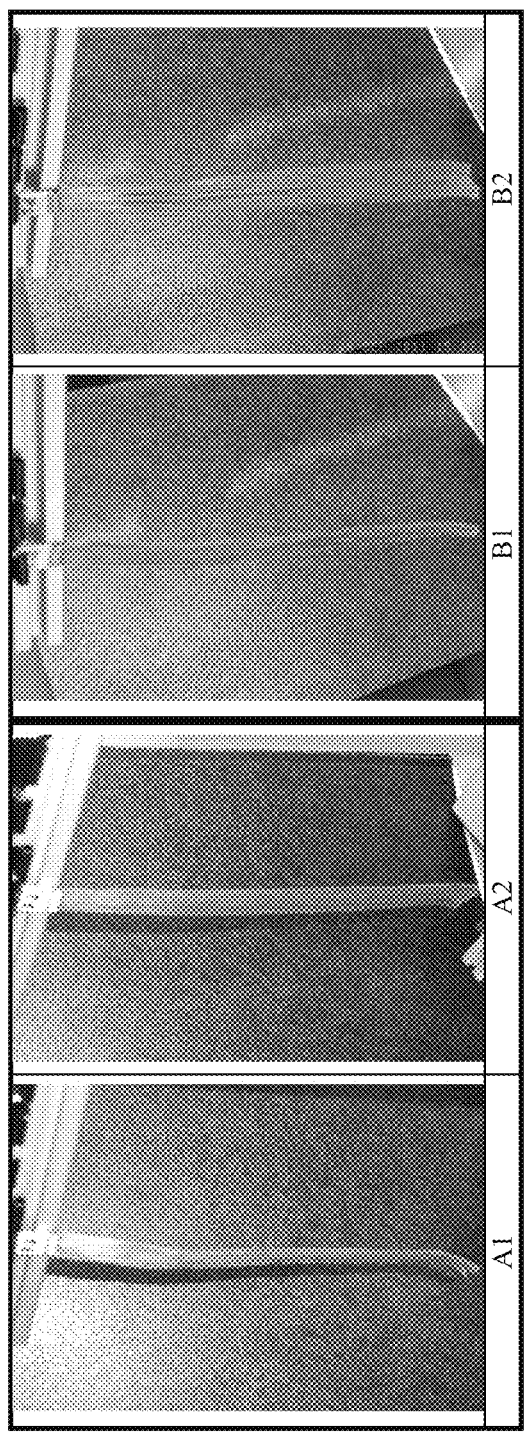

In all embodiments of the present invention, all percentages are by weight of the total composition (or formulation), unless specifically stated otherwise. All ratios are weight ratios, unless specifically stated otherwise. All ranges are inclusive and combinable. The number of significant digits conveys neither a limitation on the indicated amounts nor on the accuracy of the measurements. All numerical amounts are understood to be modified by the word "about" unless otherwise specifically indicated. Unless otherwise indicated, all measurements are understood to be made at 25° C. and at ambient conditions, where "ambient conditions" means conditions under about 1 atmosphere of pressure and at about 50% relative humidity. All such weights as they pertain to listed ingredients are based on the active level and do not include carriers or by-products that may be included in commercially available materials, unless otherwise specified. Where amount ranges are given, these normally relate to the total amount of the (class of) compound(s) specified. For example, "the composition comprises from about 0.1% to about 20% of ethylenic monomer" means that the total amount of ethylenic monomer in the composition must be within the specified range.

Herein, "comprising" means that other steps and other ingredients which do not affect the end result can be added. This term encompasses the terms "consisting of" and "consisting essentially of". The compositions, methods, uses, kits, and processes of the present invention can comprise, consist of, and consist essentially of the elements and limitations of the invention described herein, as well as any of the additional or optional ingredients, components, steps, or limitations described herein.

The term "substantially free from" or "substantially free of" as used herein means less than about 1%, less than about 0.8%, less than about 0.5%, less than about 0.3%, or about 0%, by total weight of the composition or formulation.

"Hair," as used herein, means mammalian hair including scalp hair, facial hair and body hair, more preferably hair on the human head and scalp. "Hair shaft" means an individual hair strand and may be used interchangeably with the term "hair."

"Internal region of the hair shaft," as used herein, means any non-surface portion of the hair shaft, including the inner portion of the cuticle, underneath the cuticle and the cortex. "Non-surface portion" may be understood to mean that portion of the hair that is not in direct contact with the outside environment.

"Cosmetically acceptable," as used herein, means that the compositions, formulations or components described are suitable for use in contact with human keratinous tissue without undue toxicity, incompatibility, instability, allergic response, and the like. All compositions and formulations described herein which have the purpose of being directly applied to keratinous tissue are limited to those being cosmetically acceptable.

"Derivatives," as used herein, includes but is not limited to, amide, ether, ester, amino, carboxyl, acetyl, acid, salt and/or alcohol derivatives of a given compound.

"Monomer," as used herein, means a discrete, non-polymerised chemical moiety capable of undergoing polymerisation in the presence of an initiator. "Ethylenic monomer," as used herein, means a chemical species that contains an olefinic carbon-carbon double bond (C=C) and is capable of undergoing polymerization in the presence of an initiator.

"Polymer," as used herein, means a chemical formed from the polymerisation of two or more monomers. The term "polymer" as used herein shall include all materials made by the polymerisation of monomers as well as natural polymers. Polymers made from only one type of monomer are called homopolymers. A polymer comprises at least two monomers. Polymers made from two or more different types of monomers are called copolymers. The distribution of the different monomers can be calculated statistically or block-wise— both possibilities are suitable for the present invention. Except if stated otherwise, the term "polymer" used herein includes any type of polymer including homopolymers and copolymers.

The term "molecular weight" or "M.Wt." as used herein refers to the number average molecular weight unless otherwise stated.

"Chemically modify," or grammatical equivalents thereof, as used herein, means that a chemical moiety such as monomer and/or crosslinker and/or polymer, stably affixes to a second chemical moiety, for example, a keratin protein, another component of hair, and/or another monomer or crosslinker or polymer. Normally, "chemically modify" means stably affix via a covalent bond, unless otherwise stated.

"Separately packaged," as used herein, means any form of packaging that prevents one composition or formulation from coming into physical contact, or admixing, with a second composition or formulation.

"Kit," as used herein, means a packaging unit comprising a plurality of components i.e. a kit of parts. An example of a kit is, for example, a first composition and a separately packaged second composition. Another kit may comprise application instructions comprising a method and a composition/formulation.

"Anhydrous" as used herein means that the composition comprises less than 5%, less than 3% or, less than 2%, less than 1%, or 0% water.

"Polyol" as used herein means compounds comprising at least 2 hydroxyl groups and glycol compounds including polymers thereof. Polyol includes polyether polyol compounds having a hydroxyl group at each end (i.e. both ends) of the polymer chain.

Explanation of the Invention

As described in the background, there is a need for optimised and/or tailored conditioners to be employed in methods for chemically modifying the internal region of a hair shaft. Since consumers with fine and/or limp hair particularly benefit from the mechanical changes to their hair resultant from the chemical modification—these changes resulting in improved hair volume, stylability and manageability—the first choice for experienced stylists and formulation technologists is a light conditioner rather than a more powerful or even intensive conditioner. Indeed, the latter may weight down the hair and detract from or even reduce the improved mechanical properties provided by the chemical modification. Furthermore, the stylist or technologist would be drawn toward using an oxidising agent in the light conditioner. This is because such chemical modifications usually employ an initial hair reducing step in order to open up the cuticle. This reducing step reduces the disulfide bridges between neighbouring cysteine amino acids in hair protein, thus allowing the cuticle to lift. The cuticle lifting is thought to facilitate the migration of the monomer into the hair shaft. Thus it makes sense that once the polymerisation step has been completed, for an oxidising agent to be applied to the hair in order to close the cuticle again via re-oxidation of the disulfide bridges, firstly to smoothen down the hair shaft to improve hair feel and help prevent damage to the hair due to the cuticles catching, and secondly to help 'seal in' the polymerised or attached monomers inside the hair shaft. Such oxidising agent may be hydrogen peroxide employed in the conditioner at about 0.1% to about 3% by weight. See, for example, Table III at the top of page 11 of EP-A-2295029.

Interestingly, an aspect of the present invention is the identification of a previously unrecognised problem i.e. what is known as a problem invention. Indeed, it had been noticed that occasionally the hair demonstrated increased static following the chemical modification. Static causes so-called "fly away" hair, which may reduce the increased manageability of the hair resultant from the chemical modification. The static was particularly noticeable after combing and for some hair types more than others. It had been assumed that it was caused by the chemical modification of the hair i.e. as a result of the altered mechanical properties. However, experimentation surprisingly revealed that this was not the case. As has already been alluded to, consumers prefer the chemical modification to be followed by a conditioning step. Thus, it had not been previously identified that the increased static was actually caused by the application of the finishing conditioner on the hair. This is surprising since conditioners typically smoothen hair and thus combing-induced static is reduced. In response to this finding, the experienced stylist and/or formulation technologist is to find a conditioner specifically suited to reducing static and also optimised such that the benefits of the chemical modification are not reduced or nullified. This represents a large task for the experienced stylist and/or formulation technologist, since only little information is available on methods for chemically modifying hair employing ethylenic monomers. Vis-à-vis reducing the static, the formulation technologist may consider: U.S. Pat. No. 4,719,104 (Helene Curtis), where static-reducing agents are mentioned in the $2^{nd}$ half of col. 17; U.S. Pat. No. 4,726,945 (Colgate-Palmolive Co.), see col. 2, l.25-29; or U.S. Pat. No. 5,002,761 (Henkel), see $2^{nd}$ and $3^{rd}$ paragraphs of the "Description of Invention" in col. 2.

In contrast, however, the inventors surprisingly found that excellent results were achieved when the conditioning composition comprises a hydrophobic polyol and a hydrophilic polyol. Without being bound by theory, it is believed that the combination of hydrophobic polyol and a hydrophilic polyol results in these benefits because, unlike classical conditioning compositions which comprise a relatively high concentration of cationic surfactant in an aqueous solution, the conditioning composition as per the present invention comprises components that do not form a neutral complex with any predominantly anionic stably affixed and/or polymerized ethylenic monomer e.g. inside the hair the hair shaft. Such complexes may hinder the migration of the ethylenic monomer inside the hair shaft, which is not preferred. In an embodiment of the present invention, the conditioning composition as described herein is anhydrous. Indeed, it was found that improved results are generated when the composition is anhydrous. Without being bound by theory, it is believed that employing the hydrophobic polyol and a hydrophilic polyol in an anhydrous context resulted in improved results, because of the water gradient created. Moreover, the concentration of the active components in an anhydrous conditioning composition are at the maximum, due to the lack of water (i.e. solvent).

Method

The first aspect, relates to a method for chemically modifying the internal region of the hair shaft.

In an embodiment, the method comprises: applying an oxidising formulation to the hair prior to, at the same time as and/or after applying the monomer composition to the hair. In an embodiment, the oxidising formulation acts as an initiator for the chemical modification. In an embodiment, the initiator is an oxidising agent. In an embodiment, the method comprises: (a) washing the hair; then (b) applying an oxidising formulation to the hair, wherein the oxidising formulation comprises an oxidising agent selected from the group consisting of: peroxides, persulfates, and mixtures thereof; then (c) allowing the oxidising formulation to remain on the hair for a period of time y, wherein time y is from 1 min to 120 mins, or from 2 mins to 45 mins, or from 3 mins to 20 mins, or from 4 mins to 10 mins; then (d) de-wetting the hair; then (e) applying a monomer composition to the hair, wherein the monomer composition comprises an ethylenic monomer having a molecular weight of 500 g/mole or less, or from about 50 g/mole to about 500 g/mole, or from about 75 g/mole to about 400 g/mole; then (f) allowing the monomer composition to remain on the hair for a period of time x, wherein the time x is from 1 min to 120 mins, or from 2 mins to 45 mins, or from 3 mins to 20 mins, or from 4 mins to 10 mins; (g) washing the hair; then (h) applying a conditioning composition to the hair, wherein the conditioning composition comprises a hydrophobic polyol and a hydrophilic polyol. In an embodiment, the oxidising agent is the initiator.

The method may comprise de-wetting the hair. In an embodiment the de-wetting the hair comprises the application of an absorbent material to the hair such that wetness is transferred from the hair to the absorbent material and wherein the wetness comprises the cosmetically acceptable carrier. The absorbent material may be selected from the group consisting of: towel, absorbent paper, and combinations thereof. In an embodiment, the de-wetting the hair comprises allowing moisture to evaporate from the hair wherein the moisture comprises the cosmetically acceptable carrier. In an embodiment, the de-wetting the hair comprises towel drying the hair such that the oxidising formulation no longer drips from the hair. In an embodiment, the de-wetting the hair comprises removing superficial oxidising formulation from the hair. In an embodiment, the de-wetting the hair does not comprise rinsing the oxidising formulation from the hair. The de-wetting the hair may last for time z, wherein time z is from about 1 min to about 120 mins, from about 2 mins to about 45 mins, from about 3 mins to about 20 mins, or from about 4 mins to about 10 mins.

In an embodiment, the method is for chemically modifying the internal region of the hair shaft. In an embodiment, the chemically modifying is selected from the group consisting of: the formation of a polymer in the internal region of the hair shaft; the modification of the internal region of the hair shaft with a polymer; and combinations thereof. In an embodiment, the chemically modifying the internal region of the hair shaft is polymerisation in the internal region of the hair shaft. In an embodiment, the polymerisation that occurs is free radical polymerisation.

In an embodiment, the method provides a performance benefit selected from the group consisting of: increased hair volume, increased hair fullness, increased hair bounciness, increased hair movement, improved hair feel, improved hair mobility, improved hair texture, improved hair appearance of health, increased control over hairstyle, improved desired hair shape retention, improved hairstyle durability, improved hair shine, more tamed hair, increased curl definition, more defined-looking hair, improved humidity resistance, and combinations thereof. In an embodiment, the performance benefit is still noticeable to at least about 40% of consumers after about 15 washes, or to at least about 45% of consumers, or to at least about 50% of consumers, or to at least about 55% of consumers, or to at least about 60% of consumers, or to at least about 65% of consumers, or to at least about 70% of consumers. In an embodiment, the consumers are selected from the group consisting of: consumers that regularly style their hair and have thin and/or limp hair, and consumers that regularly style their hair and have thick and/or unruly hair.

Monomer Composition

According to the first aspect, the monomer composition comprises an ethylenic monomer having a molecular weight of about 500 g/mole or less. In an embodiment, the ethylenic monomer comprises a vinyl group. "Vinyl group" as used herein, means $H_2C=CH-R$. In an embodiment, the ethylenic monomer comprises an acrylate group or a methacrylate group. "Acrylate group" as used herein, means $H_2C=CH-C(O)O-R$. Acrylic acid, for example, comprises an acrylate group since R is hydrogen. "Methacrylate group" as used herein means $H_2C=C(CH_3)-C(O)O-R$. In an embodiment, the ethylenic monomer is selected from the group consisting of: mesaconic acid, 2-pentenoic acid, tiglic acid, tiglic acid esters, furan-3-acrylic acid, 2-acrylamido-2-methyl-1-propanesulfonic acid, maleamic acid, 3-aminocrotonic acid, crotonic acid esters, itaconic anhydride, trimethylsilylacrylate, poly(ethylene glycol)acrylates, N-vinylacetamide, 2-acetamidoacrylic acid, vinylsulfonic acid, tetrahydrofurfurylacrylate, N-methyl-N-vinylacetamide, vinylpropionate, vinylanisole, vinylcrotonate, methyl 3-hydroxy-2-methylenebutyrate, methacryloyl-L-lysine, N-(2-hydroxypropyl)methacrylamide, 2-acrylamidodiglycolic acid, 2-ethoxyethyl acrylate, 2-butoxyethyl acrylate, N-isopropylmethacrylamide, 2-aminoethyl methacrylate, 2-bromoethyl acrylate, 3-(dimethylamino)propyl acrylate, (3-acrylamidopropyl)trimethyl ammonium salt, [2-(acryloyloxy)ethyl]-trimethylammonium salt, alkylacetamidoacrylate, sulfoalkyl(meth)acrylate, 3-sulfopropyl acrylate, 3-sulfopropyl methacrylate, derivatives thereof, and mixtures thereof. In an embodiment, the monomer composition comprises at least one ethylenic monomer, selected from the group cited above, as the sole ethylenic monomer(s). In an embodiment, the ethylenic monomer is selected from the group consisting of 3-sulfopropyl acrylate, 3-sulfopropyl methacrylate, and salts, derivatives and mixtures thereof. In an embodiment, the only ethylenic monomer(s) present are selected from the group consisting of 3-sulfopropyl acrylate, 3-sulfopropyl methacrylate, salts or derivatives thereof, and mixtures thereof. In an embodiment, the sole ethylenic monomer is 3-sulfopropyl acrylate. In an embodiment, the ethylenic monomer is 3-sulfopropyl acrylate, which is added to the monomer composition as 3-sulfopropyl acrylate potassium salt.

In an embodiment, the ethylenic monomer is selected from the group consisting of: acrylic acid, sodium acrylate, potassium acrylate, calcium acrylate, monoethanolamine acrylate, 3-hydroxypropyl acrylate, 2,5-butylaminoethyl acrylate, methacrylic acid, sodium methacrylate, potassium methacrylate, calcium methacrylate, monoethanolamine methacrylate, 2-N,N-dimethylaminoethyl acrylate, glycidyl methacrylate, 2-dimethylamino ethyl methacrylate, 2-hydroxypropyl methacrylate, 3-hydroxypropyl methacrylate, 2,4-dihydroxybutyl methacrylate, 2,3-epoxybutyl methacrylate, 2-t-butylaminoethyl methacrylate, 2-(2-diethylamino)ethyl methacrylate, ethylene glycol mono methacrylate, itaconic acid (and salts thereof), vinyl pyridine, resorcinol, and mixtures thereof. In an embodiment, the sole ethylenic monomer is acrylic acid. In an embodiment, the ethylenic monomer is acrylic acid and wherein the monomer composition comprises from about 0.1% to about 20% total amount of ethylenic monomer.

The molecular weight of the ethylenic monomer is important because of the need for the monomer to penetrate into the hair shaft prior to polymerisation. Large and/or bulky monomers would penetrate less easily into the hair shaft. In an embodiment, the ethylenic monomer has a molecular weight of from about 50 g/mole to about 500 g/mole, or from about 75 g/mole to about 400 g/mole, or from about 100 g/mole to about 400 g/mole, or from about 150 g/mole to about 300 g/mole. In an embodiment, the ethylenic monomer does not have a molecular weight of below about 50 g/mole, or below about 75 g/mole, or below about 100 g/mole, or below about 150 g/mole, or above about 500 g/mole, or not above about 400 g/mole, or not above about 300 g/mole. In an embodiment, the monomer composition comprises from about 0.1% to about 20%, or from about 1% to about 15%, or from about 5% to about 14%, or from about 7% to about 13%, or about 11% to about 12.5%, of ethylenic monomer. This amount may be the total amount of ethylenic monomer in the composition. In an embodiment, two or more different ethylenic monomers are present in the monomer composition pursuant to the first aspect. The resultant polymers may be copolymers.

In an embodiment, the monomer composition comprises an inhibitor compound selected from the group consisting of: 2-tert-butyl-4-hydroxy-anisole, 3-tert-butyl-4-hydroxy-anisole, and mixtures thereof. The inhibitor compound may be present in the monomer composition in an amount of from about 1 milligram to about 1000 milligram per kilogram of the ethylenic monomer. Such amount may be the total amount of inhibitor compound being those selected from the group consisting of: 2-tert-butyl-4-hydroxy-anisole, 3-tert-butyl-4-hydroxy-anisole. In an embodiment, the inhibitor compound is present in the monomer composition in an amount of from about 50 milligram to about 800 milligram, or from about 100 milligram to about 500 milligram, or from about 100 milligram to about 300 milligram, or from about 100 milligram to about 200 milligram, per kilogram of ethylenic monomer. In an embodiment, the inhibitor compound is the mixture of 2-tert-butyl-4-hydroxy-anisole and 3-tert-butyl-4-hydroxy-anisole. In an embodiment, the mixture of 2-tert-butyl-4-hydroxy-anisole and 3-tert-butyl-4-hydroxy-anisole comprises greater than 50%, or greater than 60%, or greater than 80% 3-tert-butyl-4-hydroxy-anisole.

The inhibitor compound functions as a polymerisation inhibitor i.e. it stabilises the ethylenic monomer so that it does not polymerise prior to contact with an inhibitor. The inhibitor compound provides excellent performance in that the ethylenic monomer is effectively stabilised and also when the ethylenic monomer exposed to an initiator, the ethylenic monomer polymerises efficiently and quickly. In an embodiment, the monomer composition is substantially free of a polymer derived from the polymerisation of ethylenic monomers.

Other polymerisation inhibitors used for stabilising ethylenic monomers are known in the art e.g. 4-methoxy phenol. In an embodiment, the monomer composition comprises less than about 500 ppm, or less than about 400 ppm, or less than about 300 ppm, or less than about 200 ppm, or less than about 100 ppm, or less than about 50 ppm, or less than about 10 ppm, of 4-methoxy phenol. In an embodiment, the monomer composition is substantially free of a polymerisation inhibitor, with the exception of an inhibitor compound selected from the group consisting of: 2-tert-butyl-4-hydroxy-anisole, 3-tert-butyl-4-hydroxy-anisole, and mixtures thereof.

The monomer composition may comprise a crosslinker having a molecular weight suitable to penetrate the hair shaft. The purpose of the crosslinker is to covalently bond the monomer to the hair, and/or monomer to other monomer, and/or and polymer to other polymer. The molecular weight of the crosslinker may be about 500 g/mole or less, or from about 100 g/mole to about 500 g/mole, or from about 100 g/mole to about 400 g/mole, or from about 200 g/mol to about 400 g/mole. The crosslinkers may be selected from the group consisting of: 1,4-bisacryloylpiperazine, methylenebisacrylamide, ethylenebisacrylamide, divinylbenzene, polyethylene glycol di(meth)acrylate, ethylene glycol di(meth)acrylate, 1,3-butanediol di(meth)acrylate, 1,4-butanediol di(meth)acrylate, neopentyl glycol di(meth)acrylate, bis[2-(methacryloyloxy)ethyl]phosphate, N,N'-bis(acryloyl)cystamine, N,N-diallylacryalmide, triallyl cyanurate, 3-(acryloyloxy)-2-hydroxypropyl methacrylate, and mixtures thereof.

The monomer composition and/or oxidising formulation may comprise a viscosity-increasing agent. Viscosity is important when the composition is in the form of gel, cream, lotion, emulsion etc because it prevents the composition from sliding off the skin and/or hair. However, lower viscosities allow actives to penetrate/diffuse more easily e.g. into the internal region of the hair shaft. The viscosity of the monomer composition when it is in the form of a gel may be from about 500 mPa·s to about 15000 mPa·s, or from about 1000 mPa·s to about 10000 mPa·s, or from about 1500 mPa·s to about 7500 mPa·s, or from about 2000 mPa·s to about 5000 mPa·s, measured with a Brookfield Viscosimeter RVDV III Ultra CP 52 at 25° C. and 1 rpm. The viscosity-increasing agent may be selected from the group consisting of non-ionic thickeners, cationic thickeners, anionic thickeners, amphoteric thickeners, and mixtures thereof. The viscosity-increasing agent may be present in the monomer composition in an amount of from about 0.1% to about 10%, or from about 0.2% to about 5.0%. In an embodiment, the monomer composition comprises a non-ionic or anionic thickener (or mixtures thereof), which is in view of the typically anionic chemistry of any polymerised ethylenic monomer. Non-ionic or anionic thickeners are less likely to interact directly with any formed polymer and hence the formation of insoluble complexes or precipitates is also less likely. In an embodiment, the viscosity-increasing agent is stable at the required pH and does not substantially affect the active levels of ethylenic monomer. The viscosity-increasing agent may be a cross-linked or a non-crosslinked polymer.

In an embodiment, the viscosity-increasing agent is a hydrophobically-modified polyacrylate polymer. Such hydrophobically-modified polyacrylate polymers are particularly suitable when the composition/formulation is created by the addition of at least one salt. The composition may comprise from about 0.5% to about 1.5% of the hydrophobically-modified polyacrylate polymer, by total weight of the composition. Suitable hydrophobically-modified polyacrylate polymers include: acrylates/C10-C30 alkylacrylates copolymers such as Ultrez® 20/21 from Lubrizol, and Permulen® TR1 from Lubrizol; acrylates/beheneth-25 methacrylate copolymers such as Aculyn® 28 from Rohm & Haas; acrylates/ceteth-20 itaconate copolymers such as Structure® 3001 or 2001 from Akzo Nobel.

In an embodiment, the viscosity-increasing agent is a non-crosslinked associative thickening polymer. The monomer composition or oxidising formulation may comprise from about 0.5% to about 3% of the non-crosslinked associative thickening polymer, by total weight of the composition. Suitable associative thickeners include polyurethane-based polymers such as polyurethane-30 e.g. LuvigelSTAR® from BASF. Also EO-PO-block copolymers may be useful, for example Pluronics® from BASF.

In an embodiment, the viscosity-increasing agent comprises at least one polysaccharide. In an embodiment, the monomer composition comprises a heteropolysaccharide. The total polysaccharide present in the monomer composition may be from about 0.2% to about 5%, or from about 0.5% to about 4%, by total weight of the composition. Suitable polysaccharides and heterosaccharides include starches and derivatives thereof, e.g. mono- or di-esters with phosphoric acid, cellulose types and their derivatives, xanthan gums, carrageenans. Preferred heteropolysaccharides include xanthan gum such as Keltrol® T from Kelco, and Natrosol® 250 HHR from Herkules. In an embodiment, the polysaccharide is selected from the group consisting of hydroxyethylcellulose, hydroxypropylcellulose, xanthan gum, carrageenans, and mixtures thereof. Xanthan gums and derivatives thereof are present in an amount of from about 0.2% to about 1.5%, or from about 0.5% to about 0.9%, by total weight of the composition. Starches and derivatives thereof are present in an amount of from about 3% to about 4% by total weight of the composition. A preferred starch is hydroxypropyl starch phosphate such as Structure® XL from National Starch. In an embodiment, the monomer composition comprises two different polysaccharide viscosity-increasing agents.

The monomer composition, conditioning composition, and/or oxidising formulation may further comprise a cosmetically acceptable carrier, wherein said composition/formulation may comprise from about 60% to about 99.9%, or from about 70% to about 95%, or from about 80% to about 90%, of a cosmetically acceptable carrier, by total weight of the composition or formulation. The carrier may comprise water. In an embodiment, the carrier comprises water, fatty alcohols, volatile organic alcohols, and mixtures thereof. In an embodiment the carrier is water.

In an embodiment, the monomer composition further comprises a cation and an anion; wherein the cation is selected from the group consisting of inorganic cations having a charge density of 0.05 charge/picometer or more, or about 0.052 charge/picometer or more. In an embodiment the inorganic cation is a metal. In an embodiment, the cation may not be selected from inorganic cations having a charge density of about 0.04 charge/picometer or less, or less than about 0.05 charge/picometer. In an embodiment, the cation is selected from the group consisting of inorganic cations having a charge density of about 0.050 charge/picometer to about 0.090 charge/picometer, or from about 0.052 charge/picometer to about 0.080 charge/picometer, or to about 0.070 charge/picometer, or to about 0.060 charge/picometer, or to about 0.053 charge/picometer. The charge density of an ion is calculated by dividing the charge by the ionic radius which results in charge per picometer, the charge density. For example, $Sr^{2+}$ has an ionic radius of 127 pm and a charge of 2. Consequently, the charge per picometer is 0.0157 charge/pm. Ion radii of common metals can be found in Table I of EP patent application 11194611.7 with a priority date of 19 Jan. 2011 in the name of The Procter & Gamble Company. Tables of ionic radii tables can also be found in common inorganic chemistry textbooks, for example Atkins P. W., Physical Chemistry, $6^{th}$ Edition, 2001. In an embodiment, the inorganic cation has a charge of at least 2+, or at least 3+. In an embodiment, the inorganic cation is not a transition metal. In an embodiment, the inorganic cation is not a metal capable of cleaving hydrogen peroxide. In an embodiment, the inorganic cation is $Al^{3+}$. The molar ratio of the cation to the monomer (i.e. cation:monomer) may be from about 1:10 to about 2:1, or from about 1:5 to about 3:2, or from about 1:2 to about 1:1, or from about 1:3 to about 1:1. The molar amount of cation is preferred to be in excess of the molar amount of counterion of the ethylenic monomer when the ethylenic monomer is added into the composition in the form of a salt. The inorganic cation may also be present in the oxidising formulation. In an embodiment, the oxidising formulation comprises a cation, wherein the cation is not selected from inorganic cations having a charge density of about 0.04 charge/picometer or less, or less than about 0.05 charge/picometer. In an embodiment, the oxidising formulation comprises a cation, wherein the cation is selected from the group consisting of inorganic cations having a charge density of about 0.05 charge/picometer or more, and the cation is present in an amount of from about 0.001% to about 2%, or from about 0.01% to about 1%, or from about 0.04% to about 0.2%, by total weight of the oxidising formulation.

In an embodiment, the anion may be selected from the group consisting of sulfate, sulfonate, phosphate, nitrate, chloride, citrate, lactate, formate, and mixtures thereof. In an embodiment, the anion may be selected from the group consisting of sulfate, sulfonate, and mixtures thereof. In an embodiment, the anion is sulfate. In an embodiment, the molar ratio of the cation to the anion (cation:anion) is from about 1:5 to about 5:1, or from about 1:4 to about 3:1, or from about 2:3 to about 3:2. Where the inorganic metal cation is $Al^{3+}$ and the anion is sulfate, the molar ratio of the cation to the anion is about 2:3.

In an embodiment, the monomer composition comprises an oxidising agent. In an embodiment, the monomer composition comprises hydrogen peroxide. Indeed, the oxidising agent may function as an initiator for the e polymerisation and thus mixed into the monomer composition immediately prior to application onto hair. In an embodiment, the monomer composition is substantially free of oxidising agents and/or initiators. This may be the case when the hair has already been treated with an oxidising agent and/or initiator. In another embodiment, the monomer composition is substantially free of oxidising agents selected from the group consisting of: peroxides; persulfates; and mixtures thereof. In another embodiment, the monomer composition is substantially free of a lactone or an alpha-methylene lactone compound. In another embodiment, the monomer composition is in ready-to-use form, wherein ready-to-use form means that no pre-mixing is required prior to application onto hair. In another embodiment, the monomer composition is substantially free of at least one of the following: a reducing agent, a transition metal.

Oily compounds may aid the penetration of the ethylenic monomer into the skin and/or scalp, which may not be preferred. In an embodiment, the monomer composition is substantially free of oily compounds. In another embodiment, the monomer composition and the oxidising formulation are substantially free of oily compounds.

Oxidising Formulation

In an embodiment, the method comprises applying an oxidising formulation to the hair. The oxidising formulation comprises an oxidising agent. The oxidising agent may be selected from the group consisting of: peroxides; persulfates; and mixtures thereof. In an embodiment, the oxidizing agent is hydrogen peroxide. Another composition or formulation as mentioned herein, or a plurality thereof, may comprise at least one oxidising agent. In an embodiment, the monomer composition does not comprise an oxidising agent.

The oxidising agent may be present in an amount of from about 0.01% to about 15%, by total weight of the composition/formulation. When a persulfate oxidising agent is used, it may be in powder form and mixed as a liquid immediately prior to application onto hair. The final amount of persulfate in the composition/formulation may be from about 0.5% to about 2%, or 0.8% to about 1.2%. When the oxidising agent is a peroxide, the peroxide may be present in an amount of from about 0.5% to about 5%, from about 1% to about 4%, from about 1.3% to about 3%, or from about 1.5% to about 3%.

In an embodiment, for example, after applying the oxidising formulation to the hair but prior to de-wetting the hair, the oxidising formulation is allowed to remain on the hair for a period of time y, wherein time y is from about 1 min to about 120 mins, from about 2 mins to about 45 mins, from about 3 mins to about 20 mins, or from about 4 mins to about 10 mins.

When the oxidising formulation comprises peroxide, the oxidising formulation may comprise a buffer system to stabilise the pH. Suitable buffers may also act as chelating agents. Chelation of transition metals, for example copper or iron from pipes which might be present in trace amounts in tap water, is important because peroxides are sensitive to cleavage by transition metals. In the absence of a buffer system the transition metal may cleave the peroxide, deactivating it. Typical buffer systems comprise a strong acid and its weak conjugate base or a weak base and its conjugate acid. An example of a suitable buffer system is phosphoric acid and disodium phosphate. Another example of a suitable buffer system is citric acid and sodium hydroxide. In an embodiment, the monomer composition comprises a buffer system.

Conditioning Composition

The conditioning composition comprises both a hydrophobic polyol and a hydrophilic polyol. It is believed that hydrophobic polyols provide conditioning benefits such as moisturizing and facilitated deposition of oily conditioning agents when included. In an embodiment, the conditioning composition comprises from about 10% to about 40%, or from about 15% to about 25%, or from 18% to about 21% of hydrophobic polyol. This amount is useful for providing improved conditioning benefits while providing acceptable stickiness. This amount may be the total amount of hydrophobic polyol in the conditioning composition. In an embodiment, the hydrophobic polyol has a solubility in water at 25° C. of less than about 1 g/100 g water, less than about 0.5 g/100 g water, or less than about 0.1 g/100 g water. In an embodiment, the hydrophobic polyol has an HLB value of from about 1 to less than about 10, or from about 2 to about 8. The hydrophobic polyol may be liquid at 25° C. In an embodiment, the hydrophobic polyol is selected from the group consisting of: polypropylene glycols having a molecular weight of from about 200 g/mol to about 100 000 g/mol, $C_2$-$C_{22}$ alkyl ether of polypropylene glycols, polyethylene glycol/polypropylene glycol copolymers, $C_2$-$C_{22}$ alkyl ether of polyethylene glycol/polypropylene glycol copolymers, and mixtures thereof. In an embodiment, the hydrophobic polyol is a polypropylene glycol. In an embodiment, the hydrophobic polyol is a polypropylene glycol having a molecular weight of from about 200 g/mol to about 100 000 g/mol, from about 500 g/mol to about 60 000 g/mol, or from about 1000 g/mol to about 10 000 g/mol. This is in view of providing excellent conditioning benefits, having certain required water solubility and compatibility with hydrophilic polyols.

In an embodiment, the conditioning composition comprises from about 15% to about 85%, from about 20% to about 80%, from about 25% to about 75%, or from about 45% to about 55% of hydrophilic polyol. The amount is useful for providing a desired viscosity and spreadability of the composition and in view of providing a carrier in for the conditioning composition and used for generating a heat when mixed with water where the conditioning composition is anhydrous. This amount may be the total amount hydrophilic polyol in the conditioning composition. In an embodiment, the conditioning composition comprises a weight ratio of hydrophobic polyol to hydrophilic polyol of from about 1:1 to about 1:50, or from about 1:1.5 to about 1:25, or from about 1:2 to about 1:10. The ratio is useful for providing moisturising benefit and helping the deposition of oily conditioning agents when included in the composition. In an embodiment, the sum of the hydrophobic polyol and the hydrophilic polyol in the conditioning composition is from about 50% to about 98%, or from about 65% to 75%. This is in view of the desired viscosity and spreadability of the composition. The sum may be the total of all hydrophobic polyol and hydrophilic polyol present. The hydrophilic polyol may be liquid at 25° C. In an embodiment, the hydrophilic polyol has a solubility in water at 25° C. of more than about 1 g/100 g water, or more than about 2 g/100 g water, or more than about 5 g/100 g water. In an embodiment, the hydrophilic polyol has an HLB value of about 10 or more.

In an embodiment, the hydrophilic polyol is selected from the group consisting of: polyethylene glycol, propylene glycol, butylene glycol, hexylene glycol, glycerin, diglycerin, diethylene glycol, dipropylene glycol, and mixtures thereof. In an embodiment, the hydrophilic polyol is selected from the group consisting of: polyethylene glycol, propylene glycol, butylene glycol, hexylene glycol, glycerin, diglycerin, and mixtures thereof.

In an embodiment, the hydrophilic polyol is a polyethylene glycol. Polyethylene glycol is useful due to its ability to generate a heat by mixing with water and its physical properties such as viscosity and fluidity. In an embodiment, the polyethylene glycol is a liquid at 25° C. and has the formula:

$$H(OCH_2CH_2)_n\text{—OH}$$

wherein n has an average value of from 4 to 12. This polyethylene glycol is also known as a polyethylene oxide, and polyoxyethylene. In an embodiment, the polyethylene glycol is PEG-200 wherein n has an average value of about 4. Commercially available PEG-200 is e.g. trade name Carbowax PEG-200 available from Union Carbide. In an embodiment, the polyethylene glycol is a high molecular weight polyethylene glycol, such as those having the formula: $H(OCH_2CH_2)_n$—OH, wherein n has an average value of from 2000 to 14000, from about 5000 to about 9000, or from about 6000 to about 8000. In an embodiment, the polyethylene glycol is selected from the group consisting of: PEG-2M wherein n has an average value of about 2000 (PEG-2M is also known as Polyox WSR® N-10 from Union Carbide and also as PEG-2000); PEG-5M wherein n has an average value of about 5000 (PEG-5M is also known as Polyox WSR® N-35 and as Polyox WSR® N-80, both from Union Carbide and as PEG-5000 and PEG 300 000); PEG-7M wherein n has an average value of about 7000 (PEG-7M is also known as Polyox WSR® N-750 from Union Carbide); PEG-9M wherein n has an average value of about 9000 (PEG-9M is also known as Polyox WSR® N-3333 from Union Carbide); PEG-14M wherein n has an average value of about 14000 (PEG-14M is also known as Polyox WSR® N-3000 from Union Carbide); and mixtures thereof.

In an embodiment, the conditioning composition is anhydrous. In an embodiment, the conditioning composition is anhydrous and comprises an inorganic heat generating agent which generates a heat by mixing with water and wherein the conditioning composition warms to a temperature of from about 26° C. to about 80° C. upon mixing with water. The conditioning composition can warm by a heat from the hydrophilic polyol mixing with water and/or warm by a heat from an inorganic heat generating agent mixing with water if this is included. In an embodiment, the conditioning composition warms to a temperature of from about 26° C. to about 80° C., from about 30° C. to about 60° C., or from about 35° C. to about 45° C. This temperature can be adjusted by, for example, the amount of the hydrophilic polyol, the addition, type and/or amount of inorganic heat generating agent, and additional agents which can control the heat generating reaction. It is believed that warming cosmetic compositions such as hair care compositions can provide enhanced efficacy, i.e., can provide improved benefits. In an embodiment, the inorganic heat generating agent is selected from the group consisting of: chlorides such as calcium chloride ($CaCl_2$, $CaCl_2.H_2O$, $CaCl_2.2H_2O$), magnesium chloride ($MgCl_2$, $MgCl_2.2H_2O$, $MgCl_2.4H_2O$), aluminium chloride ($AlCl_3$, $AlCl_3.6H_2O$), ferric chloride ($FeCl_3$, $FeCl_3.2H_2O$), and zinc chloride ($ZnCl_2$); sulfates such as magnesium sulfate ($MgSO_4$, $MgSO_4.H_2O$, $MgSO_4.4H_2O$), zinc sulfate ($ZnSO_4.H_2O$), ferrous sulfate ($FeSO_4$, $FeSO_4.H_2O$), aluminium sulfate ($Al(SO_4)_3$), calcium sulfate ($CaSO_4$, $CaSO_4.\frac{1}{2}H_2O$, $CaSO_4.H_2O$), and sodium sulfate ($Na_2SO_4$); dry alum; calcium oxide (CaO); magnesium oxide (MgO); sodium carbonate ($Na_2CO_3$); zeolite; and sodium hydrogen phosphate ($Na_2HPO_4$). In an embodiment, the inorganic heat generating agent is selected from the group consisting of: anhydrous inorganic salts such as sodium sulfate ($Na_2SO_4$), calcium sulfate ($CaSO_4$), magnesium sulfate ($MgSO_4$), aluminium sulfate ($Al(SO_4)_3$), calcium chloride ($CaCl_2$), magnesium chloride ($MgCl_2$), calcium oxide (CaO), and mixtures thereof, this is in view of their effective heat generation, mildness to hair and/or skin, and easy handling. In an embodiment, the inorganic heat generating agent is anhydrous magnesium sulfate ($MgSO_4$). In an embodiment, the inorganic heat generating agent is in particulate form. The inorganic heat generating agent may have an average diameter of from about 0.01 micron to about 40 micron, from about 0.05 micron to about 30 micron, or from about 0.1 micron to about 20 micron, in view of preventing gritty feel. In an embodiment, the conditioning composition comprises from about 5% to about 60%, from about 5% to about 50%, from about 10% to about 45%, or from about 12% to about 20% of inorganic heat generating agent. In an embodiment, the conditioning composition is substantially free of inorganic heat generating agent. In an embodiment, the conditioning composition comprises a carrier being water. An embodiment being substantially free of inorganic heat generating agent and/or comprising a carrier being water has the advantage that the composition is easier, faster and thus more economic to manufacture.

In an embodiment, the conditioning composition comprises an oily conditioning agent. The oily conditioning agent provides conditioning benefits such as softness and smoothness. In an embodiment, the oily conditioning agent is liquid at 25° C. In an embodiment, the conditioning composition comprises an oily conditioning agent, wherein the oily conditioning agent is liquid at 25° C., and is selected from the group consisting of a paraffin, an ester, a silicone, a fatty compound, and mixtures thereof. In an embodiment, the oily conditioning agent has a solubility in water at 25° C. of less than about 1 g/100 g water, less than about 0.5 g/100 g water, or less than about 0.1 g/100 g water. In an embodiment, the conditioning composition comprises from about 0.1% to about 20%, from about 1% to about 10%, from about 2% to about 10% of an oily conditioning agent. This amount may be the total amount of oily conditioning agent in the conditioning composition. In an embodiment, the oily conditioning agent provides is selected from the group consisting of: paraffins, esters, silicones, fatty compounds, mineral oils, hydrocarbons, poly α-olefin oils, vegetable oils, and mixtures thereof.

In an embodiment, the oily conditioning agent is an ester. In an embodiment, the ester has a melting point of less than 25° C. In an embodiment, the ester is selected from the group consisting of: pentaerythritol ester oils, trimethylol ester oils, citrate ester oils, glyceryl ester oils, and mixtures thereof. In an embodiment, the ester is selected from the group consisting of: pentaerythritol ester oils and trimethylol ester oils being pentaerythritol tetraisostearate, pentaerythritol tetraoleate, trimethylolpropane triisostearate, trimethylolpropane trioleate, and mixtures thereof. Such compounds are available from Kokyo Alcohol with tradenames KAKPTI, KAKTTI, and Shin-nihon Rika with tradenames PTO, ENUJERUBU TP3SO. In an embodiment, the ester is a citrate ester oils. Examples of esters are: triisocetyl citrate with tradename CITMOL 316 available from Bernel, triisostearyl citrate with tradename PELEMOL TISC available from Phoenix, and trioctyldodecyl citrate with tradename CITMOL 320 available from Bernel, triisostearin with tradename SUN ESPOL G-318 available from Taiyo Kagaku, triolein with tradename CITHROL GTO available from Croda Surfactants Ltd., trilinolein with tradename EFADERMA-F available from Vevy, or tradename EFA-GLYCERIDES from Brooks.

In an embodiment, the oily conditioning agent is a silicone. In an embodiment, the oily conditioning agent is a silicone oil. Silicone oils are useful in view of their conditioning benefits such as softness and smoothness. The silicone can include volatile or non-volatile silicone conditioning agents. In an embodiment, the silicone has a viscosity of from about 5 to about 2 000 000 cSt, from about 500 to about 1 800 000 cSt, from about 5 000 to about 1 500 000 cSt, or from about 10 000 to about 1 300 000 cSt, measured at 25° C. The viscosity can be measured at 25° C. by means of a glass capillary viscometer as set forth in Dow Corning Corporate Test Method CTM0004, Jul. 20, 1970, which is incorporated by reference herein in its entirety. "cSt" means centistokes(s).

In an embodiment, the silicone is selected from the group consisting of: polydimethylsiloxane, polydiethylsiloxane, polymethylphenylsiloxane, and mixtures thereof. In an embodiment, the silicone is polydimethylsiloxane, which is also known as dimethicone. These silicone compounds are available, for example, from GE Toshiba Silicones, from the General Electric Company in their Viscasil® and SF 96 series, and from Dow Corning in their Dow Corning 200 series. Dimethicones having a viscosity of about 10 000 cSt can be purchased from GE Toshiba Silicones with a tradename TSF451-1MA.

In an embodiment, the silicone is a silicone gum. The term "silicone gum", as used herein, means a polyorganosiloxane material having a viscosity at 25° C. of greater than or equal to 1 000 000 cSt. It is recognized that the silicone gums described herein can also have some overlap with the above-disclosed silicone compounds. This overlap is not intended as a limitation on any of these materials. Silicone gums are described by Petrarch, and others including U.S. Pat. No. 4,152,416, to Spitzer et al., issued May 1, 1979 and Noll, Walter, Chemistry and Technology of Silicones, New York: Academic Press 1968. Also describing silicone gums are General Electric Silicone Rubber Product Data Sheets SE 30, SE 33, SE 54 and SE 76. All of these described references are incorporated herein by reference in their entirety. In an embodiment, the silicone gum has a mass molecular weight in excess of about 200 000, or between about 200 000 and about 1 000 000. In an embodiment, the silicone gum is selected from the group consisting of: polydimethylsiloxane, poly (dimethylsiloxane methylvinylsiloxane) copolymer, poly (dimethylsiloxane diphenylsiloxane methylvinylsiloxane) copolymer and mixtures thereof. In an embodiment, the conditioning composition comprises a mixture of silicone gum and cyclomethicone, wherein such mixture may have a viscosity of from about 5 000 to about 100 000 cSt.

In an embodiment, the silicone is a polyalkyleneoxide-modified siloxane selected from the group consisting of polypropylene oxide modified and polyethylene oxide modified polydimethylsiloxane. These materials are also known as dimethicone copolyols. In an embodiment, the silicone is an amino-substituted siloxane being an amodimethicone. In an embodiment, the silicone is an amino-substituted siloxane being a trimethylsilylamodimethicone. Examples of amino-substituted siloxanes are those having the tradename "UCAR SILICONE ALE 56" available from Union Carbide.

In an embodiment, the oily conditioning agent is a fatty compound having a melting point of less than 25° C. In an embodiment, the fatty compound is selected from the group consisting of: unsaturated fatty alcohols having from about 10 to about 30 carbon atoms, unsaturated fatty acids having from about 10 to about 30 carbon atoms, fatty acid derivatives, fatty alcohol derivatives, and mixtures thereof. In an embodiment, the fatty compound is a fatty alcohol having from about 10 to about 30 carbon atoms, from about 12 to about 22 carbon atoms, or from about 16 to about 22 carbon atoms. In an embodiment, the fatty alcohols are unsaturated and have straight or branched chains. In an embodiment, the fatty alcohol is selected from the group consisting of: oleyl alcohol, isostearyl alcohol, tridecylalcohol, decyl tetradecyl alcohol, and octyl dodecyl alcohol, and mixtures thereof. These fatty alcohols are available, for example, from Shinnihon Rika.

In an embodiment, the conditioning composition comprises a polyoxyalkylene derivative. In an embodiment, the conditioning composition comprises a polyoxyalkylene derivative and an inorganic heat generating agents. It is believed that polyoxyalkylene derivatives can help the dispersion of inorganic heat generating agents and thus prevent the agglomeration of inorganic heat generating agents, which can cause a gritty feel to the skin and/or hair. Also polyoxyalkylene derivative can provide slippery feel to the hair. In an embodiment, the conditioning composition comprises from about 0.1% to about 10%, from about 0.5% to about 10%, or from about 1% to about 5% polyoxyalkylene derivative. This amount may be the total amount of polyoxyalkylene derivative in the composition. In an embodiment, the polyoxyalkylene derivative is a water-soluble polyoxyalkylene derivative. In an embodiment, the polyoxyalkylene derivative is selected from the group consisting of: polyoxyethylene/polyoxypropylene copolymers, polyoxyethylene alkyl ethers, polyoxypropylene alkyl ethers, polyoxyethylene alkyl ether esters, polyoxypropylene alkyl ether esters, polyoxyethylene glyceryl esters, polyoxypropylene glyceryl esters, and mixtures thereof. In an embodiment, the polyoxyalkylene derivative is a polyoxyethylene/polyoxypropylene copolymer.

In the conditioning composition, the hydrophilic polyol may be used as a carrier. In an embodiment, the conditioning composition comprises a carrier other than the hydrophilic polyol. The additional carriers useful herein are liquid carriers and include; for example, liquid paraffin; mineral oil; vegetable oil; ester oil such as pentaerythritol tetraisostearate; and mixtures thereof. In an embodiment, the conditioning composition comprises from about 25% to about 90%, or from about 30% to about 85% of additional carrier.

In an embodiment, the conditioning composition comprises a viscosity-modifying agent. In an embodiment, the viscosity modifying agent is selected from the group consisting of: vinyl polymers such as cross linked acrylic acid polymers with the CTFA name Carbomer, carboxylic acid/carboxylate copolymers such as acrylic acid/alkyl acrylate copolymers with the CTFA name Acrylates/C10-30 Alkyl Acrylate Crosspolymer, cellulose derivatives and modified cellulose polymers, polyvinylpyrrolidone, polyvinyl alcohol, guar gum, other gums, starch-based polymers, alginic acid-based polymers, acrylate polymers, polyalkylene glycols having a molecular weight of more than about 1000, inorganic water soluble material such as bentonite, aluminium magnesium silicate, laponite, hectorite, and anhydrous silicic acid, and mixtures thereof. In an embodiment, the viscosity modifying agent is hydroxypropyl cellulose and/or hydroxyethyl cellulose. In an embodiment, the conditioning composition comprises from about 0.01% to about 5%, from about 0.05% to about 3%, or from about 0.1% to about 3% of a viscosity modifying agent. This amount may be the total amount of viscosity modifying agent in the composition. In an embodiment, the conditioning composition comprises a total of from about 0.01% to about 5%, from about 0.05% to about 3%, or from about 0.1% to about 3% of hydroxypropyl cellulose and/or hydroxyethyl cellulose.

In an embodiment, the conditioning composition comprises a high melting point fatty compound. In an embodiment, the high melting point fatty compound has a melting point of at least 25° C., at least 35° C., at least 45° C., or at least 55° C., and is selected from the group consisting of fatty alcohols, fatty acids, fatty alcohol derivatives, fatty acid derivatives, and mixtures thereof. Nonlimiting examples of the high melting point compounds are found in International Cosmetic Ingredient Dictionary, Fifth Edition, 1993, and CTFA Cosmetic Ingredient Handbook, Second Edition, 1992. In an embodiment, the conditioning composition comprises from about 0.1% to about 30%, from about 0.2% to about 25%, from about 0.5% to about 15% of a high melting point fatty compound. This amount may be the total amount of high melting point fatty compound in the composition. In an embodiment, the high melting point fatty compound is a fatty alcohol and is selected from the group consisting of cetyl alcohol, stearyl alcohol, behenyl alcohol, and mixtures thereof. In an embodiment, the conditioning composition comprises a total of from about 0.1% to about 30%, from about 1% to about 10%, or from about 2% to about 7% of cetyl alcohol, stearyl alcohol, behenyl alcohol or a mixtures thereof. In an embodiment, the conditioning composition comprises a total of from about 0.1% to about 30%, or from about 1% to about 10%, or from about 2% to about 7% of cetyl alcohol, stearyl alcohol, behenyl alcohol or a mixtures thereof. Commercially available high melting point fatty compounds useful herein include: cetyl alcohol, stearyl alcohol, and behenyl alcohol having tradenames KONOL series available from Shin Nihon Rika (Osaka, Japan), and NAA series available from NOF (Tokyo, Japan); pure behenyl alcohol having tradename 1-DOCOSANOL available from WAKO (Osaka, Japan), various fatty acids having tradenames NEO-FAT available from Akzo (Chicago Ill., USA), HYSTRENE available from Witco Corp. (Dublin Ohio, USA), and DERMA available from Vevy (Genova, Italy).

In an embodiment, the conditioning composition comprises a cationic surfactant. In an embodiment, the conditioning composition comprises from about 0.1% to about 10%, from about 0.25% to about 8%, from about 0.5% to about 5%, or from about 1% to about 3% of cationic surfactant. This amount may be the total amount of cationic surfactant in the composition. In an embodiment, the cationic surfactant is selected from the group consisting of: behenyl trimethyl ammonium chloride (available, for example, with tradename INCROQUAT TMC-80 from Croda and ECONOL TM22 from Sanyo Kasei), distearyl dimethyl ammonium chloride (available, for example, with tradename Varisoft TA 100 from Goldschmidt), cetyl trimethyl ammonium chloride (available, for example, with tradename CA-2350 from Nikko Chemicals), hydrogenated tallow alkyl trimethyl ammonium chloride, dialkyl (14-18) dimethyl ammonium chloride, ditallow alkyl dimethyl ammonium chloride, dihydrogenated tallow alkyl dimethyl ammonium chloride, dicetyl dimethyl ammonium chloride, di(behenyl/arachidyl)dimethyl ammonium chloride, dibehenyl dimethyl ammonium chloride, stearyl dimethyl benzyl ammonium chloride, stearyl propyleneglycol phosphate dimethyl ammonium chloride, stearoyl amidopropyl dimethyl benzyl ammonium chloride, stearoyl amidopropyl dimethyl(myristylacetate) ammonium chloride, N-(stearoyl colamino formyl methy) pyridinium chloride, and mixtures thereof. In an embodiment, the cationic surfactant is selected from the group consisting of: behenyl trimethyl ammonium chloride and behenyl trimonium chloride, and wherein the conditioning composition comprises a total of from about 0.5% to about 5%, or from about 1% to about 3% of these compounds. In an embodiment, the conditioning composition comprises di-(alkyl carboxyethyl) hydroxyethyl methylammonium methosulfate (with a tradename Rewoquat V3620 available from Goldschmidt), and/or methyl bis-(alkylamidoethyl) 2-hydroxyethylammonium methosulfate (with a tradename Varisoft 222 LT-90 available from Goldschmidt). In an embodiment, the conditioning composition comprises a salt of an amidoamine and an acid. This is in view of their conditioning function as a cationic surfactant. In an embodiment, the amidoamine has the general formula:

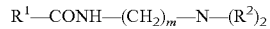

$$R^1—CONH—(CH_2)_m—N—(R^2)_2$$

wherein $R^1$ is a residue of $C_{11}$ to $C_{24}$ fatty acids, $R^2$ is a $C_1$ to $C_4$ alkyl, and m is an integer from 1 to 4. In an embodiment, the amidoamine is selected from the group consisting of: stearamidopropyldimethylamine, stearamidopropyldiethylamine, stearamidoethyldiethylamine, stearamidoethyldimethylamine, palmitamidopropyldimethylamine, palmitamidopropyldiethylamine, palmitamidoethyldiethylamine, palmitamidoethyldimethylamine, behenamidopropyldimethylamine, behenamidopropyldiethylamine, behenamidoethyldiethylamine, behenamidoethyldimethylamine, arachidamidopropyldimethylamine, arachidamidopropyldiethylamine, arachidamidoethyldiethylamine, arachidamidoethyldimethylamine, and mixtures thereof. In an embodiment, the amidoamine is selected from the group consisting of: stearamidopropyldimethylamine, stearamidoethyldiethylamine, and mixtures thereof. Commercially available amidoamines useful herein include: stearamidopropyldimethylamine having tradename SAP-DMA available from Inolex, and tradename Amidoamine MPS available from Nikko. In an embodiment, the acid is selected from the group consisting of l-glutamic acid, lactic acid, hydrochloric acid, malic acid, succinic acid, acetic acid, fumaric acid, l-glutamic acid hydrochloride, tartaric acid, and mixtures thereof. In an embodiment, the acid is selected from the group consisting of: l-glutamic acid, lactic acid, hydrochloric acid, and mixtures thereof. The acid may be contained at a level such that the mole ratio of amidoamine to acid is, preferably from about 1:0.3 to about 1:1, more preferably from about 1:0.5 to about 1:0.9. Commercially available acids include: l-Glutamic acid (cosmetic grade) available from Ajinomoto.

In an embodiment, the conditioning composition comprises a non-ionic surfactant, in view of providing improved physical stability. In an embodiment, the conditioning composition comprises from about 0.01% to about 10%, from about 0.05% to about 8%, or from about 0.1% to about 5% of non-ionic surfactant. The non-ionic surfactant useful herein includes, for example, polyoxyethylene glyceryl esters such as PEG-modified triglycerides with tradenames Tagat TO® available from Goldschmidt Chemical Corporation, PEG-60 hydrogenated castor oil, and PEG-100 stearate; ethylene glycol ethers of fatty alcohols such as ceteareth-20; alkyl polysaccharide surfactants such as alkyl polyglycosides; long chain tertiary amine oxides such as lauramine oxide; and long chain tertiary phosphine oxides such as lauryl dimethyl phosphine oxide. In an embodiment, the conditioning composition comprises a polyoxyethylene glyceryl ester and/or a ethylene glycol ethers of fatty alcohol.

The conditioning composition may include other additional components, which may be selected by the artisan according to the desired characteristics of the final product and which are suitable for rendering the composition more cosmetically or aesthetically acceptable or to provide them with additional usage benefits. Other additional components generally are used individually at levels of from about 0.001% to about 10%, or up to about 5% of the conditioning composition.

In an embodiment, the conditioning composition comprises by weight: (i) from about 2% to about 60%, or from about 15% to about 25%, or from about 18% to about 21%, of the hydrophobic polyol; (ii) from about 15% to about 85%, or from about 25% to about 75%, or from about 45% to about 55%, of the hydrophilic polyol; (iii) from about 0.1% to about 20%, of an oily conditioning agent; (iv) from about 0.1% to about 10% of a cationic surfactant; (v) from about 5% to about 60%, of an inorganic heat generating agent which generates a heat by mixing with water; and (vi) from about 0.1% to about 10%, of a polyoxyalkylene derivative.

In an embodiment, the conditioning composition comprises by weight: (i) from about 15% to about 22% of a hydrophobic polyol being PPG-34 (PEG-4); (ii) from about 40% to about 55% of a hydrophilic polyol being polyethylene glycol 200; (iii) from about 0.1% to about 8% of oily conditioning agents, wherein the conditioning composition comprises both a dimethicone and a fatty alcohol; (iv) from about 0.1% to about 10% of a cationic surfactant being a mixture of behentrimonium chloride and cetrimonium chloride; (v) from about 5% to about 17% of an inorganic heat generating agent being anhydrous magnesium sulfate; and (vi) from about 0.1% to about 10% of a polyoxyalkylene derivative being a polyethylene/polypropylene block copolymer.

In an embodiment, the conditioning composition comprises by weight: (i) from about 15% to about 22% of a hydrophobic polyol being a polypropylene glycol; (ii) from about 40% to about 55% of a hydrophilic polyol being a polyethylene glycol; (iii) from about 0.1% to about 8% of oily conditioning agents; (iv) from about 0.1% to about 10% of a cationic surfactant; and (v) from about 0.1% to about 10% of a polyoxyalkylene derivative being a polyethylene/polypropylene block copolymer; and wherein the conditioning composition is substantially free of inorganic heat generating agent.

Other Aspects

According to the second aspect, the present invention relates to a kit for chemically modifying the internal region of the hair shaft comprising:
  (I). an oxidising formulation, wherein the oxidising formulation comprises an oxidising agent being hydrogen peroxide;
  (II). a monomer composition, wherein the monomer composition comprises an ethylenic monomer having a molecular weight of 500 g/mole or less;
  (III). a conditioning composition to the hair, wherein the conditioning composition comprises a hydrophobic polyol and a hydrophilic polyol.

In an embodiment, the oxidising formulation, monomer composition and/or conditioning composition as per the description of the monomer composition according to the first aspect.

According to the third aspect, the present invention relates to the use of the kit according to the second aspect, for chemically modifying the internal region of the hair shaft.

According to a fourth aspect, the present invention relates to the use of glycol compounds for reducing hair static. In an embodiment, the glycol compounds are a mixture of polypropylene glycol and polyethylene glycol. In an embodiment, the use is for reducing hair static following modification of the internal region of the hair shaft, preferably following chemical modification.

EXAMPLES

The following examples further describe and demonstrate embodiments within the scope of the present invention. The examples are given solely for the purpose of illustration and are not to be construed as limitations of the present invention.

| | Monomer compositions | | | | | | |
|---|---|---|---|---|---|---|---|
| | Ex. 1 | Ex. 2 | Ex. 3 | Ex. 4 | Ex. 5 | Ex. 6 | Ex. 7 |
| Purified water | QSP | QSP | QSP | QSP | QSP | QSP | QSP |
| Hydroxyethylcellulose[1] | — | 0.20 | 0.20 | 0.20 | 0.20 | 0.20 | 0.20 |
| Hydroxyethylcellulose[6] | 0.70 | — | — | — | — | — | — |
| Disodium EDTA | 0.12 | 0.12 | 0.12 | 0.12 | 0.12 | 0.12 | 0.12 |
| Xanthan gum[2] | — | 0.50 | 0.50 | 0.50 | 0.50 | 0.50 | 0.50 |
| Aluminium sulfate octadecahydrate | — | 2.40 | — | — | — | — | — |
| Sodium hydroxide | — | 0.76 | 0.76 | 0.76 | 0.76 | 0.76 | 0.76 |
| Citric acid | 0.30 | 0.30 | 0.30 | 0.30 | 0.30 | 0.30 | 0.30 |
| 2-phenoxyethanol | 1.00 | 1.00 | 1.00 | 1.00 | 1.00 | 1.00 | 1.00 |
| p-hydroxybenzoic acid methylester | 0.20 | — | — | — | — | — | — |
| Methyl parabene | — | 0.20 | 0.20 | 0.20 | 0.20 | 0.20 | 0.20 |
| Coceth-10[3] | 0.70 | 0.70 | 0.70 | 0.70 | 0.70 | 0.70 | 0.70 |
| PEG-35 castor oil[4] | 0.70 | 0.70 | 0.70 | 0.70 | 0.70 | 0.70 | 0.70 |
| Fragrance | 0.30 | 0.30 | 0.30 | 0.30 | 0.30 | 0.30 | 0.30 |
| 3-sulfopropyl acrylate potassium salt[5] | 8.00 | 10.00 | 12.00 | 12.00 | 12.00 | 12.00 | 15.00 |

Monomer compositions

|  | Ex. 1 | Ex. 2 | Ex. 3 | Ex. 4 | Ex. 5 | Ex. 6 | Ex. 7 |
|---|---|---|---|---|---|---|---|
| 2-Cert-butyl-4-hydroxy-anisole | 750 ppm | 250 ppm | 180 ppm | — | 280 ppm | 10 ppm | 10 ppm |
| 3-Cert-butyl-4-hydroxy-anisole | — | 670 ppm | 450 ppm | 950 ppm | 630 ppm | — | 270 ppm |
| Total | 100 | 100 | 100 | 100 | 100 | 100 | 100 |

KEY:

All numbers in the tables are wt % unless otherwise stated;

QSP = sufficient quantity for 100%;

[1] = Cellosize ® HEC QP-4400H from Dow Europe GmbH;

[2] = Keltrol ® CG-T from CP Kelco A HUBER COMPANY;

[3] = Genapol ® C-100 from Clariant Produkte GmbH (Deutschland);

[4] = Cremophor ® EL from BASF The Chemical Company;

[5] = 3-sulfopropyl acrylate potassium salt from Raschig.;

[6] = Natrosol ® 250 HHR from Herkules.

Conditioning Compositions

|  | Ex. 8 | Ex. 9 | Ex. 10 | Ex. 11 | Ex. 12 |
|---|---|---|---|---|---|
| Polyethylene glycol *1 | QSP | QSP | QSP | QSP | QSP |
| Propyleneglycol | 5.0 | — | — | — | — |
| Polypropylene glycol *2 | 10.0 | 10.0 | 19.3 | 19.3 | 19.3 |
| Silicone oil *3 | — | 1.0 | 4.2 | 4.2 | 4.2 |
| Ester oil *4 | 2.0 | — | — | — | — |
| Anhydrous magnesium sulfate ($MgSO_4$) | 15.0 | 25.0 | 15.0 | — | 15.0 |
| Polyethylene/polypropylene block copolymer *5 | 3.0 | 3.0 | 3.0 | 3.0 | 3.0 |
| Cetyl Alcohol *6 | 1.0 | 3.6 | 1.0 | 1.0 | 1.0 |
| Stearyl Alcohol *7 | 1.8 | 6.1 | 1.8 | 1.8 | 1.8 |
| Behenyl trimonium chloride *8 | 2.0 | 2.0 | 0.8 | 0.8 | 0.8 |
| Distearyl dimethyl ammonium chloride *9 | — | 2.0 | 0.8 | 0.8 | 0.8 |
| Di-(alkyl carboxyethyl) hydroxyethyl methylammonium methosulfate *10 | 1.7 | — | 1.7 | — | 1.7 |
| Stearamidopropyl Dimethylamine *11 | — | — | 0.8 | 0.8 | — |
| l-Glutamic acid *12 | — | — | 0.25 | 0.25 | — |
| Hydroxyethylcellulose *13 | — | — | 0.5 | — | — |
| PEG modified glyceride *14 | — | 5.0 | — | 5.0 | — |
| Perfume | 0.3 | 0.3 | 0.3 | 0.3 | 0.3 |
| Methyl paraben | 0.2 | 0.2 | 0.2 | 0.2 | 0.2 |
| Propyl paraben | 0.1 | 0.1 | 0.1 | 0.1 | 0.1 |
| 3-pyridinecarboxy acid amide | 0.05 | 0.05 | 0.05 | 0.05 | — |
| dl-Alpha tocopherol acetate | 0.05 | 0.05 | 0.05 | 0.05 | — |
| Hydrolyzed collagen *15 | 0.01 | 0.01 | 0.01 | 0.01 | — |
| Panthenol *16 | 0.05 | 0.05 | 0.05 | 0.05 | — |
| Panthenyl Ethyl Ether *17 | 0.05 | 0.05 | 0.05 | 0.05 | — |
| Octyl methoxycinnamate | 0.09 | 0.09 | 0.09 | 0.09 | — |
| Benzophenone-3 | 0.09 | 0.09 | 0.09 | 0.09 | — |

KEY:

*1: Polyethylene glycol: Carbowax PEG-200 available from Union Carbide;

*2: Polypropylene Glycol: PPG-34 having a tradename PP2000 available from Sanyo Kasei;

*3: Silicone oil: Dimethicone having a viscosity of about 10,000 centistokes having a tradename TSF451-1MA available from GE Toshiba Silicone;

*4: Ester oil: Pentaerythritol Tetraisostearate having a tradename KAK PTI available from Kokyu alcohol;

*5: Polyethylene/polypropylene block copolymer: Poloxamer 338 having a tradename Newpol PE-108 available from Sanyo Chemical;

*6: Cetyl Alcohol: Konol series available from Shin Nihon Rika;

*7: Stearyl Alcohol: Konol series available from Shin Nihon Rika;

*8 Behenyl trimonium chloride: Econol TM-22 available from Sanyo Kasei.

*9: Distearyl dimethyl ammonium chloride: Varisoft TA100 available from Goldschmidt;

*10: Di-(alkyl carboxyethyl) hydroxyethyl methylammonium methosulfate: Rewoquat V3620 available from Goldschmidt;

*11: Stearamidopropyl Dimethylamine: SAPDMA available from Inolex;

*12: l-Glutamic acid: l-Glutamic acid (cosmetic grade) available from Ajinomoto;

*13: Hydroxyethylcellulose: Natrosol 250 MBR available from Hercules;

*14: PEG modified glyceride: Tagat TO available from Goldschmidt;

*15: Hydrolyzed collagen: Peptein 2000 available from Hormel;

*16: Panthenol: available from Roche;

*17: Panthenyl Ethyl Ether: available from Roche.

Experimental

Experiments are carried out vis-à-vis the invention and the results can be found in the Figures.

FIG. 1-7: In test A, after the treatment method is completed, the hair strands are dried at 45° C. and take a photograph (A1). Then place the hairs of the strand between two fingers and run the fingers down the strand in a quick motion 5 times ("stroking") and then take a second photograph of the strand (A2). In test B, after the treatment method is completed, the hair is dried for 2 hours at 45° C. is combed after treatment and take a photograph (B1). Then comb the strand with a plastic comb 5 times and take a photograph (B2). The results from these experiments are shown in the Figures. The conclusions are as follows:

| FIG. | Static* |
|---|---|
| 1 | o |
| 2 | o |
| 3 | - - - |
| 4 | + + |
| 5 | + |
| 6 | - |
| 7 | + + + |

*: o = standard level;
+, + +, + + + = increasingly less static than standard;
-, - -, - - - = increasingly more static than standard.

$^{14}$C-Experiments

Introduction: The aim of this study is to study the polymerisation reaction of 3-sulfopropylacrylate (3-SPA) that takes place inside hair. A $^{14}$C-radio-labelled version (labelled C-atom:★) of 3-SPA is used:

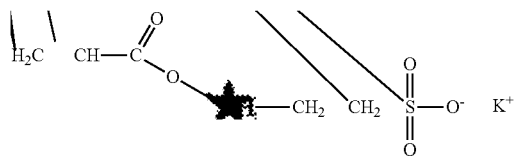

Procedure: Bundles of exactly 20 hair fibres are double bleached. The bundles are treated with either normal 3-SPA or the $^{14}$C-labelled version. The kind of treatment was according to the method:

- 10 min pre-treatment formulation (2% $H_2O_2$)
- "Towel" drying (paper tissue)
- 30 min treatment with 3-SPA in water or in hair treatment formulation
- Either rinsing with water or not.

The exact procedure for each particular hair bundle is done as follows:

| Sample | 10 min pre-treatment | Test Preparation | Rinse | Exposure Time |
|---|---|---|---|---|
| Bundle A | Yes | Blank: Non labelled 3-SPA in water | No | 30 min |
| Bundle B | Yes | $^{14}$C-3-SPA in water | No | 30 min |
| Bundle C | Yes | $^{14}$C-3-SPA in water | Yes | 30 min |
| Bundle D | Yes | $^{14}$C-3-SPA in treatment formulation | No | 30 min |
| Bundle E | Yes | $^{14}$C-3-SPA in treatment formulation | Yes | 30 min |

The detection of the $^{14}$C-3-SPA in the hair strands is carried out by micro-autoradiography. The hair strands are cut to 1.5 cm lengths and the cross-section of the strands are exposed to a silver halide photographic emulsion for 4 weeks in a dark room. The photographic film was developed and photographs thereof are taken using a microscope. Beta particles convert the silver halide into metallic silver, which is observable as black dots.

Results (representative photos shown in FIG. 8):

| Hair Bundle | Average Ag-Grain Intensity | Silver Grain Distribution |
|---|---|---|
| A (blank) | ++ | Cuticle and cortex |
| B | +++ | Cuticle and cortex |
| C | +++ | Cuticle and cortex |
| D | ++++ | Cuticle and cortex |
| E | +++ | Cuticle and cortex |

Figure 8:
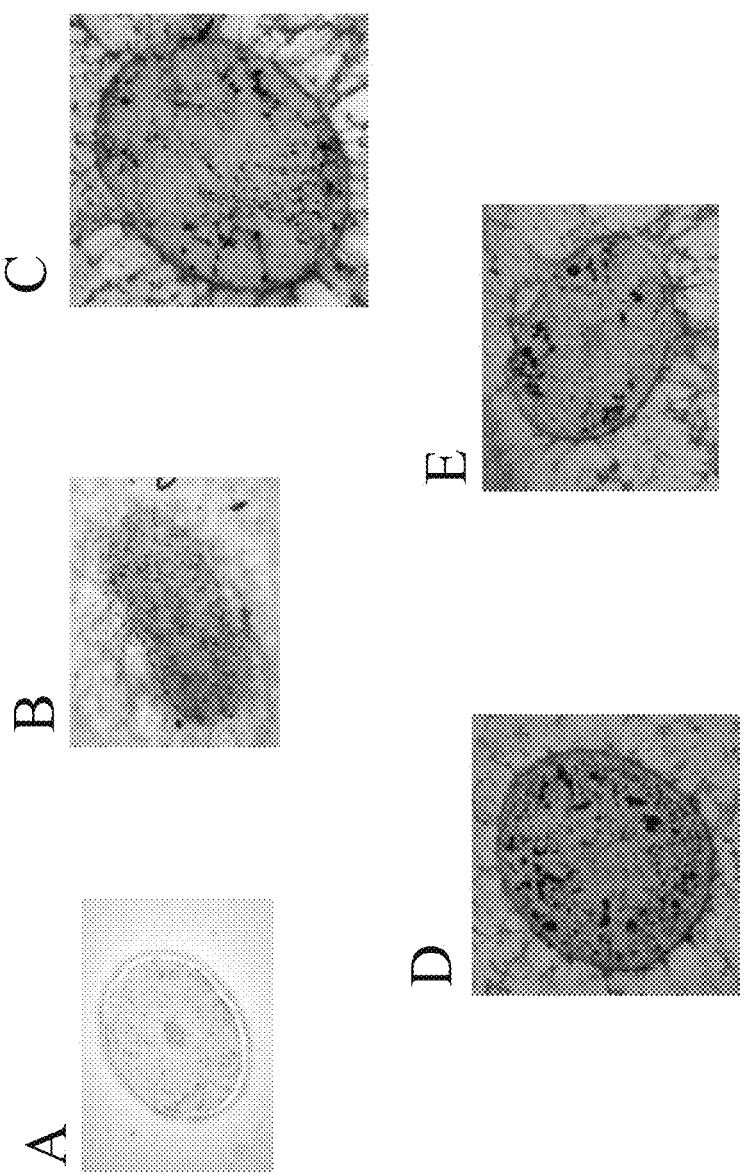
FIGS. 8A, 8B, 8C, 8D, and 8E: Photomicrographs from the carbon-14 experiments (×400 magnification).

Interpretation and Discussion of FIG. 8: All hair strands which are treated with labelled 3-SPA, show clearly that radioactive material permeates not only the hair cuticle but also considerable parts of the cortex. A mostly widely homogeneous (circular) distribution is also seen. What is even more conclusive than the high concentration of silver grains, is their accumulation at the outer half of the diffusion-passage. All pictures show a preference for accumulation in the outer part of the cortex, but for Bundle D there is even a kind of border line in the inner cortex area visible. This gives a strong hint that the silver particles really represent penetration behaviour of the 3-SPA monomer and not an artefact, for instance due to the cutting process. From the pictures in FIG. 8, it is not so clear that rinsing has no influence on the result. However, expert opinion of this technique is that the rinsing step had only low impact on the radioactivity inside the hair. This is another hint that the treatment according to the present invention is not merely a surface effect.

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm"

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A method for chemically modifying the internal region of the hair shaft, comprising:
   (a) washing the hair; then
   (b) applying an oxidising formulation to the hair, wherein the oxidising formulation comprises an oxidising agent selected from the group consisting of: peroxides, persulfates, and mixtures thereof; then
   (c) allowing the oxidising formulation to remain on the hair for a period of time y, wherein time y is from 1 min to 120 mins; then
   (d) de-wetting the hair; then
   (e) applying a monomer composition to the hair, wherein the monomer composition comprises an ethylenic monomer wherein the ethylenic monomer is 3-sulfopropyl acrylate potassium salt; and wherein the monomer composition comprises an inhibitor compound selected from the group consisting of: 2-tert-butyl-4-hydroxy-anisole, 3-tert-butyl-4-hydroxy-anisole, and mixtures thereof, then rinsing the hair, wherein the method comprises applying an initiator to the hair prior to rinsing the hair wherein the initiator initiates the chemical modification and wherein the initiator is an oxidizing agent; wherein the ethylenic monomer is present in the monomer composition in an amount of from about 5% to about 14% by total weight of the composition, wherein the monomer composition is substantially free of a reducing agent, a transition metal and the monomer composition comprises hydroxyethyl cellulose; then
   (f) allowing the monomer composition to remain on the hair for a period of time x, wherein the time x is from 1 min to 120 mins;
   (g) washing the hair; then
   (h) applying a conditioning composition to the hair, wherein the conditioning composition comprises by weight:
      (i) from about 2% to about 60% of polypropylene glycol;
      (ii) from about 15% to about 85% of polyethylene glycol;
      (iii) from about 0.1% to about 20% of an oily conditioning agent, where in the oily conditioning agent is a mixture of cetyl alcohol and stearyl alcohol;
      (iv) from about 0.1% to about 10% of a cationic surfactant wherein the cationic surfactant is selected from the group consisting of behenyl trimonium chloride, distearyl dimethyl ammonium chloride and Di-(alkyl carboxyethyl) hydroxyethyl methylammonium methosulfate;
      (v) from about 5% to about 60% of anhydrous magnesium sulfate; and
      (vi) from about 0.1% to about 10% of a polyethylene/polypropylene block copolymer.

* * * * *